(12) United States Patent
Aqad et al.

(10) Patent No.: US 10,831,100 B2
(45) Date of Patent: Nov. 10, 2020

(54) IODINE-CONTAINING PHOTOACID GENERATORS AND COMPOSITIONS COMPRISING THE SAME

(71) Applicant: ROHM AND HAAS ELECTRONIC MATERIALS LLC, Marlborough, MA (US)

(72) Inventors: Emad Aqad, Northborough, MA (US); James W. Thackeray, Braintree, MA (US)

(73) Assignee: ROHM AND HAAS ELECTRONIC MATERIALS, LLC, Marlborough, MA (US)

( * ) Notice: Subject to any disclaimer, the term of this patent is extended or adjusted under 35 U.S.C. 154(b) by 0 days.

(21) Appl. No.: 15/817,864

(22) Filed: Nov. 20, 2017

(65) Prior Publication Data
US 2019/0155152 A1   May 23, 2019

(51) Int. Cl.
   *G03F 7/004*   (2006.01)
   *C07D 333/76*   (2006.01)
   (Continued)

(52) U.S. Cl.
   CPC .......... *G03F 7/0045* (2013.01); *C07C 25/02* (2013.01); *C07C 65/05* (2013.01); *C07C 309/12* (2013.01);
   (Continued)

(58) Field of Classification Search
   CPC . G03F 7/0045; G03F 7/26; G03F 7/16; G03F 7/039; G03F 7/038; G03F 7/2004;
   (Continued)

(56) References Cited

U.S. PATENT DOCUMENTS 7,569,324 B2   8/2009  Kobayashi et al.
7,955,777 B2   7/2011  Seshimo et al.
              (Continued)

FOREIGN PATENT DOCUMENTS

JP        04338585 A      11/1992
JP     2003267968 A       9/2003
              (Continued)

OTHER PUBLICATIONS

English translation of JP, 2010-265226 A (2010) from machine translation from AIPN Japan Patent Office National Center for Industrial Property Information and Training, generated Feb. 28, 2019, 75 pages. (Year: 2010).*
              (Continued)

*Primary Examiner* — Cynthia Hamilton
(74) *Attorney, Agent, or Firm* — Cantor Colburn LLP

(57) ABSTRACT

A photoacid generator compound having formula (I):

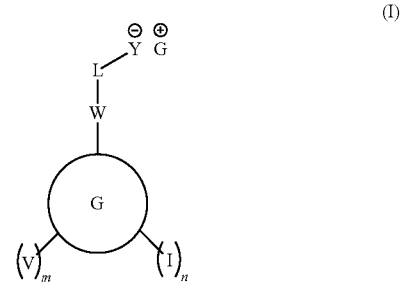

wherein, in formula (I), groups and variables are the same as described in the specification.

13 Claims, 4 Drawing Sheets

(51) Int. Cl.

| | | |
|---|---|---|
| *C07C 309/12* | (2006.01) | |
| *C07C 65/05* | (2006.01) | |
| *C07C 25/02* | (2006.01) | |
| *G03F 7/26* | (2006.01) | |
| *C07C 323/03* | (2006.01) | |
| *G03F 7/038* | (2006.01) | |
| *G03F 7/039* | (2006.01) | |
| *G03F 7/16* | (2006.01) | |
| *G03F 7/20* | (2006.01) | |
| *C07C 323/09* | (2006.01) | |
| *C07C 381/12* | (2006.01) | |
| *G03F 7/32* | (2006.01) | |

(52) U.S. Cl.
CPC .......... *C07C 323/03* (2013.01); *C07C 323/09* (2013.01); *C07C 381/12* (2013.01); *C07D 333/76* (2013.01); *G03F 7/038* (2013.01); *G03F 7/039* (2013.01); *G03F 7/0392* (2013.01); *G03F 7/0397* (2013.01); *G03F 7/16* (2013.01); *G03F 7/20* (2013.01); *G03F 7/2004* (2013.01); *G03F 7/26* (2013.01); *G03F 7/322* (2013.01)

(58) Field of Classification Search
CPC ....... C07C 323/09; C07C 25/02; C07C 65/05; C07C 309/12; C07C 323/03; C07D 333/76
See application file for complete search history.

(56) References Cited

U.S. PATENT DOCUMENTS

| | | | |
|---|---|---|---|
| 9,023,581 B2 | 5/2015 | Kawaue et al. | |
| 2002/0051927 A1 | 5/2002 | Fukushige et al. | |
| 2010/0119974 A1 | 5/2010 | Hada et al. | |
| 2010/0143830 A1 | 6/2010 | Ohashi et al. | |
| 2010/0297560 A1 | 11/2010 | Seshimo et al. | |
| 2011/0112306 A1* | 5/2011 | Nagamori | C07C 25/18 548/435 |
| 2011/0143279 A1* | 6/2011 | Shimokawa | G03F 7/0045 430/270.1 |
| 2011/0313190 A1 | 12/2011 | Nagamori et al. | |
| 2012/0015297 A1 | 1/2012 | Komuro et al. | |
| 2014/0080058 A1 | 3/2014 | Cameron et al. | |
| 2017/0115566 A1 | 4/2017 | Hatakeyama et al. | |
| 2017/0248844 A1 | 8/2017 | Aqad et al. | |
| 2017/0351177 A1* | 12/2017 | Hatakeyama | G03F 7/0397 |
| 2017/0369616 A1* | 12/2017 | Hatakeyama | G03F 7/0045 |
| 2018/0004087 A1* | 1/2018 | Hatakeyama | G03F 7/0045 |
| 2018/0039173 A1* | 2/2018 | Hatakeyama | C07C 303/32 |
| 2018/0267402 A1 | 9/2018 | Hatakeyama et al. | |
| 2018/0267403 A1 | 9/2018 | Hatakeyama et al. | |
| 2018/0275512 A1 | 9/2018 | Hatakeyama et al. | |
| 2018/0373148 A1 | 12/2018 | Hatakeyama et al. | |
| 2019/0033716 A1 | 1/2019 | Ohashi et al. | |
| 2019/0094690 A1 | 3/2019 | Hatakeyama et al. | |
| 2019/0113844 A1 | 4/2019 | Hatakeyama et al. | |
| 2019/0113846 A1 | 4/2019 | Hatakeyama et al. | |

FOREIGN PATENT DOCUMENTS

| | | | | |
|---|---|---|---|---|
| JP | 2006162735 A | | 6/2006 | |
| JP | 2010-265226 A | * | 11/2010 | |
| JP | 2011043783 A | | 3/2011 | |
| JP | 2011081044 A | | 4/2011 | |
| JP | 2011081146 A | | 4/2011 | |
| JP | 2011252147 A | | 12/2011 | |
| JP | 2015161823 A | | 9/2015 | |
| JP | 2017111206 A | | 6/2017 | |
| JP | 2018155902 A | * | 10/2018 | ........... G03F 7/0382 |
| JP | 2018159744 A | * | 10/2018 | ........... C07C 309/31 |
| WO | WO-2006088524 A1 | * | 8/2006 | ............. C08G 69/26 |

OTHER PUBLICATIONS

English translation of JP, 2006-162735, A (2006) from machine translation from AIPN Japan Patent Office National Center for Industrial Property Information and Training, generated Feb. 28, 2019, 78 pages. (Year: 2006).*
English translation of Japanese application 2017-052453 with a filing date of Mar. 17, 2017 obtained from Global Dossier file for JP 2018-155902 A , Feb. 2020, 79 pages (Year: 2020).*
English translation of Japanese application 2017-055799 with a filing date of Mar. 22, 2017 obtained from Global Dossier file for JP 2018-159744 A , Mar. 2020, 66 pages (Year: 2020).*
Christianson et al. "High Absorbing Resists Based on Trifluoromethacrylate-Vinyl Ether Copolymers for EUV Lithography" Proc. of SPIE vol. 8682 868216 (11 pages).
Fallica et al. "Dynamic absorption coefficients of CAR and non-CAR resists at EUV" Proc. of SPIE vol. 9776, 977612 (2016) (10 pages).
Linden et al., "Bleaching Studies of Rose Bengal Onium Salts", J. Am. Chem. Soc. 1988, 110, 1257-1260.
Wen-hui et al., "Multi-Dye Photosensitization System of Xanthene Iodonium Salts", Journal of Photopolymer Science and Technology, vol. 7, No. 1, (1994), 241-250.
Zhou et al., "Photoinduced Polymerization via an Intra-Ion-Pair Electron Transfer Process", Journal of Photopolymer Science and Technology, vol. 10, No. 2 (1997), 359-362.

* cited by examiner

IODINE-CONTAINING PHOTOACID GENERATORS AND COMPOSITIONS COMPRISING THE SAME

FIELD

The present disclosure generally relates to polymer compositions including a photoacid generator. Specifically, the disclosure provides copolymers derived from a monomer including at least two iodine atoms.

BACKGROUND

Extreme ultraviolet lithography ("EUVL") is one of the leading technology options to replace optical lithography for volume semiconductor manufacturing at feature sizes <20 nm. The extremely short wavelength (13.4 nm) is a key enabling factor for high resolution required at multiple technology generations. In addition, the overall system concept scanning exposure, projection optics, mask format, and resist technology—is quite similar to that used for current optical technologies. Like previous lithography generations, EUVL consists of resist technology, exposure tool technology, and mask technology. The key challenges are EUV source power and throughput. Any improvement in EUV power source will directly impact the currently strict resist sensitivity specification. Indeed, a major issue in EUVL imaging is resist sensitivity, the lower the sensitivity, the greater the source power that is needed or the longer the exposure time that is required to fully expose the resist. The lower the power levels, the more noise affects the line edge roughness ("LER") of the printed lines.

It has been shown that EUV light absorption cross-section and secondary electron generation yield are critical factors for EUV sensitivity. One way to increase EUV photoresist sensitivity is by increasing its absorption cross-section at 13.5 nm, which is an atomic property of the material that can be theoretically calculated using known atomic absorptions. Typical atoms that make up resist materials, such as carbon, oxygen, hydrogen, and nitrogen possess very weak absorption at 13.5 nm. A fluorine atom has slightly higher absorption and has been used in the search for high EUV absorbing photoresist.

Iodine has remarkably high absorption cross-section at EUV radiation. Recent patent publication JP 2015-161823 discloses iodine-containing monomers and corresponding polymers useful for lithographic processing. However, the publication does not disclose an iodine-containing small molecule photoacid-generators. There is still a need for iodine-rich resist components that possess good solubility and that imparts improved sensitivity under EUV exposure.

SUMMARY

An embodiment provides a photoacid generator compound having formula (I):

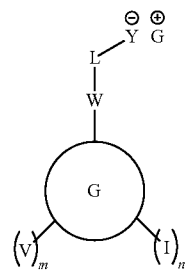

(I)

wherein, in formula (I):

"I" represents iodine;

V is $OR^1$ or $C(=O)OR^1$, wherein $R^1$ is independently H or a substituted or unsubstituted $C_{1-30}$ hydrocarbyl group optionally comprising 1 to 5 heteroatoms selected from O, S, N, P, and F, and optionally comprising an acid-cleavable group, a polymerizable group, or a combination thereof;

W is a single bond or a group selected from —(C=O)O—, —O(C=O)—, —O(SO$_2$)—, —(SO$_2$)O—, —NH(SO$_2$)—, —(SO$_2$)NH—, —NH(CO)—, —(CO)NH—, —SO$_2$—, and —SO—;

m is an integer of 0 or greater;

n is an integer of 0 or greater;

L is a single bond or a group selected from a substituted or unsubstituted $C_{1-20}$ alkylene group, a substituted or unsubstituted $C_{1-20}$ heteroalkylene group, a substituted or unsubstituted $C_{3-20}$ cycloalkylene group, and a substituted or unsubstituted $C_{3-20}$ heterocycloalkylene group, a substituted or unsubstituted $C_{6-20}$ arylene group, and a substituted or unsubstituted $C_{7-20}$ aralkylene group;

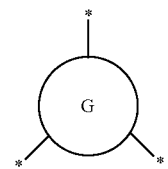

represents a monocyclic or polycyclic unsubstituted or substituted $C_{6-30}$ arylene group or a monocyclic or polycyclic unsubstituted or substituted $C_{3-30}$ heteroarylene group, wherein each "*" indicates a point of attachment to a neighboring group or atom;

$G^+$ has formula (II):

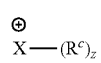

(II)

wherein, in formula (II):
X is S or I, each $R^c$ is unsubstituted or substituted, halogenated or non-halogenated and is independently a $C_{1-30}$ alkyl group; a polycyclic or monocyclic $C_{3-30}$ cycloalkyl group; a polycyclic or monocyclic $C_{4-30}$ aryl group, wherein when X is S, one of the $R^c$ is optionally attached to one adjacent $R^c$ to form a ring, wherein when X is I, n is an integer of 1 or greater, wherein when X is S, n is an integer of 0 or greater, provided the photoacid generator having formula (I) comprises at least two iodine atoms, z is 2 or 3, wherein when X is I, z is 2, or when X is S, z is 3; and Y is $SO_3$, $CO_2$, $NHSO_3$, or O.

Another embodiment provides a photoresist composition compound including the photoacid generator compound and a copolymer.

Yet another embodiment provides a method of forming an electronic device, comprising:

(a) applying a layer of the photoresist composition of claim 7 or 8 over a surface of the substrate;

(b) pattern-wise exposing the photoresist composition layer to activating radiation; and (c) developing the exposed photoresist composition layer to provide a resist relief image.

BRIEF DESCRIPTION OF THE DRAWINGS

The above and other aspects, advantages, and features of this disclosure will become more apparent by describing in further detail exemplary embodiments thereof with reference to the accompanying drawings, in which.

DETAILED DESCRIPTION

Figure 1:
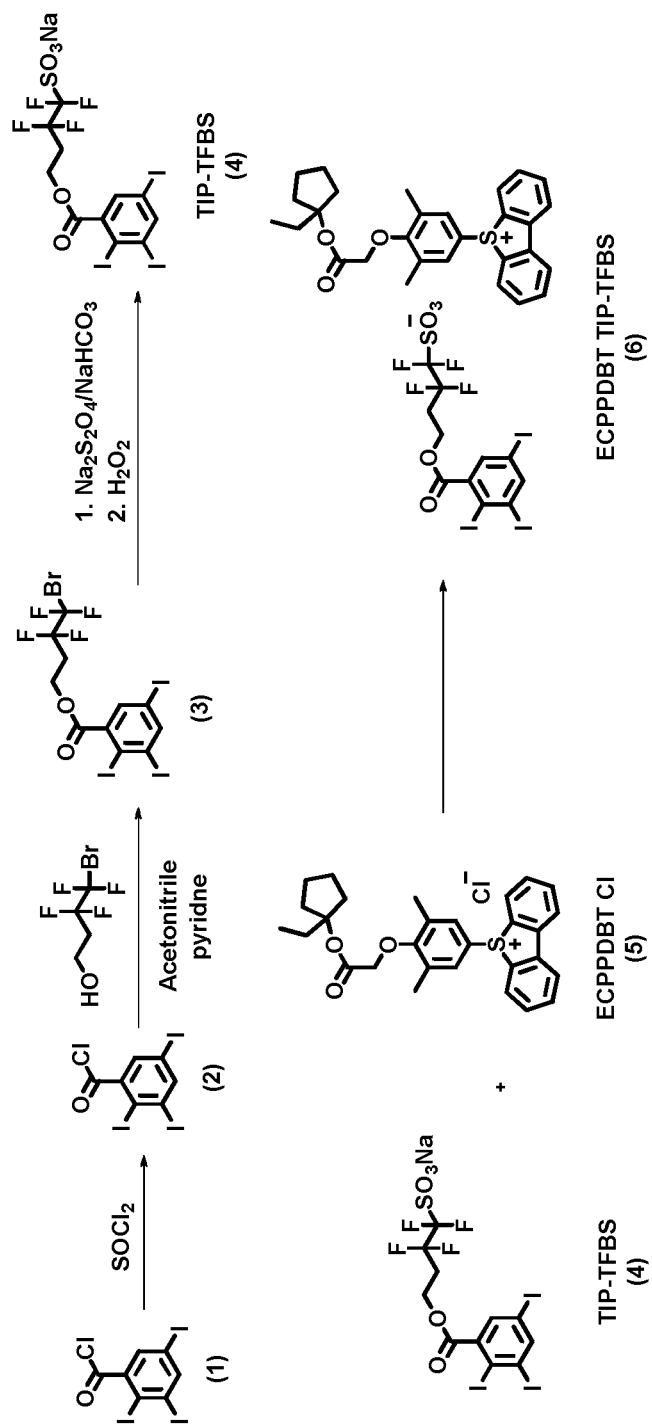
FIG. 1 is a scheme showing synthesis of the photoacid generator designated ECPPDBT TIP-TFBA.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, when a definition is not otherwise provided, the term "alkyl group" refers to a group derived from a straight or branched chain saturated aliphatic hydrocarbon having the specified number of carbon atoms and having a valence of at least one.

As used herein, when a definition is not otherwise provided, the term "fluoroalkyl group" refers to an alkyl group in which one or more hydrogen atoms are replaced with fluorine atoms.

As used herein, when a definition is not otherwise provided, the term "alkoxy group" refers to "alkyl-O—", wherein the term "alkyl" has the same meaning as described above.

As used herein, when a definition is not otherwise provided, the term "fluoroalkoxy group" refers to an alkoxy group in which one or more hydrogen atoms are replaced with fluorine atoms.

As used herein, when a definition is not otherwise provided, the term "cycloalkyl group" refers to a monovalent group having one or more saturated rings in which all ring members are carbon.

As used herein, when a definition is not otherwise provided, the term "alkenyl group" refers to a straight or branched chain, monovalent hydrocarbon group having at least one carbon-carbon double bond.

As used herein, when a definition is not otherwise provided, the term "alkenylalkyl group" refers to "alkenyl-alkyl-", wherein the terms "alkenyl" and "alkyl" have the same meaning as described above.

As used herein, when a definition is not otherwise provided, the term "alkynyl group" refers to a straight or branched chain, monovalent hydrocarbon group having at least one carbon-carbon triple bond.

As used herein, when a definition is not otherwise provided, the term "alkynylalkyl group" refers to "alkynylalkyl-", wherein the terms "alkynyl" and "alkyl" have the same meaning as described above.

As used herein, when a definition is not otherwise provided, the term "aryl", which is used alone or in combination, refers to an aromatic or heteroaromatic hydrocarbon containing at least one ring and having the specified number of carbon atoms. The term "aryl" may be construed as including a group with an aromatic or heteroaromatic ring fused to at least one cycloalkyl or heterocycloalkyl ring. The "aryl" group may include one or more heteroatom(s) independently selected from nitrogen (N), oxygen (O), P (phosphorus), and sulfur (S).

As used herein, when a definition is not otherwise provided, the term "aryloxy group" refers to "aryl-O—", wherein the term "aryl" has the same meaning as described above.

As used herein, when a definition is not otherwise provided, the term "aralkyl group" refers to a substituted or unsubstituted aryl group covalently linked to an alkyl group that is linked to a compound.

As used herein, when a definition is not otherwise provided, the term "alkylene group" refers to a straight or branched saturated aliphatic hydrocarbon group having a valence of at least two, optionally substituted with one or more substituents where indicated, provided that the valence of the alkylene group is not exceeded.

As used herein, when a definition is not otherwise provided, the term "cycloalkylene group" refers to a cyclic hydrocarbon group having a valence of at least two, optionally substituted with one or more substituents where indicated, provided that the valence of the cycloalkylene group is not exceeded.

As used herein, when a definition is not otherwise provided, the term "arylene group" refers to a functional group having a valence of at least two obtained by removal of two hydrogens in an aromatic ring, optionally substituted with one or more substituents where indicated, provided that the valence of the arylene group is not exceeded.

As used herein, when a definition is not otherwise provided, the term "aralkylene group" refers to a functional group having a valence of at least two obtained by removal of two hydrogens from the alkyl-substituted aromatic compound, optionally substituted with one or more substituents where indicated, provided that the valence of the aralkylene group is not exceeded.

As used herein, when a definition is not otherwise provided, the term "heteroarylene group" refers to a functional group having a valence of at least two obtained by removal of two hydrogens in a heteroaromatic ring, optionally substituted with one or more substituents where indicated, provided that the valence of the heteroarylene group is not exceeded.

As noted above, one way for increasing the sensitivity in EUV lithography is to increase the absorption cross-section of the resist composition at 13.5 nm. Enhancing chemically amplified resists absorption at EUV wavelength require the incorporating highly absorbing elements. The atomic absorption cross-sections at EUV of elements are known in the literature (see for example: Fallica R. et al. SPIE Advanced Lithography, 977612, 2016) and references cited therein). The elemental make up of molecules and polymers used in organic chemically amplified resists are mostly limited to carbon, hydrogen, oxygen and nitrogen. These elements have exceptionally low absorption at 13.5 nm. Fluorine atom has slightly higher absorption at 13.5 nm compared to oxygen atom. Christianson et al. explore the incorporation of fluorine atoms onto polymers backbone (see Christianson et al., SPIE Advanced Lithography 868216, 2013). The iodine atom has remarkably higher absorption cross-section at EUV. The inventors of the present invention discovered small molecules photoacid generators that include at least one aryl group substituted with one or more iodine atoms, preferably two or more iodine atoms, wherein the iodine-substituted aryl group may be a part of the photoacid generator cation, photoacid generator anion, or both.

An embodiment of the present disclosure provides a photoacid generator compound having formula (I):

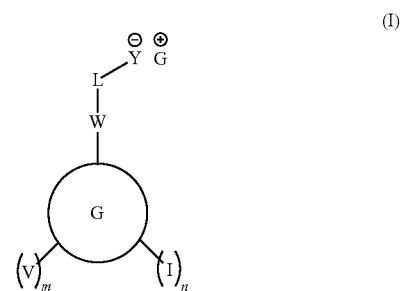

In formula (I),
"I" represents iodine, and

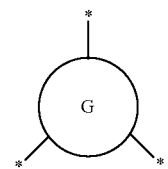

(hereinafter "G") represents a monocyclic or polycyclic unsubstituted or substituted $C_{6-30}$ arylene group or a monocyclic or polycyclic unsubstituted or substituted $C_{3-30}$ heteroarylene group, wherein each "*" indicates a point of attachment to a neighboring group or atom.

Variable n defining a number of iodines in

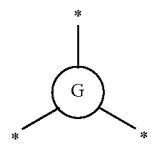

may be an integer of 0 or greater. For example, variable n may be an integer of 1 or greater. Accordingly, there may be at least one iodine atom attached to the moiety "G". In an embodiment, "G" may be a $C_6$ aryl group, and n may be 1, 2, 3, 4, or 5.

Variable m defining a number of groups V may be an integer of 0 or greater. When m is 0, group V is absent and hydrogen is present at the point of connection to the moiety "G". When m is greater than 0, V may be $OR^1$ or $C(\!=\!O)OR^1$, wherein $R^1$ is independently H or a substituted or unsubstituted $C_{1-30}$ hydrocarbyl group optionally comprising 1 to 5 heteroatoms selected from O, S, N, P, and F, and optionally comprising an acid-cleavable group, a polymerizable group, or a combination thereof. As used herein, the term "acid-cleavable group" refers to a group that is hydrolyzed by the action of an acid. Such acid-cleavable groups are well-known to one of ordinary skill in the art. In an embodiment, the acid-cleavable group may be (i) a tertiary $C_{1-30}$ alkoxy (for example, a tert-butoxy group), a tertiary $C_{3-30}$ cycloalkoxy group, a tertiary $C_{1-30}$ fluoroalkoxy group, (ii) a tertiary $C_{3-30}$ alkoxycarbonylalkyl group, a tertiary $C_{5-30}$ cycloalkoxycarbonylalkyl group, a tertiary $C_{3-30}$ fluoroalkoxycarbonylalkyl group, (iii) a tertiary $C_{3-30}$ alkoxycarbonylalkoxy group, a tertiary $C_{5-30}$ cycloalkoxycarbonylalkoxy group, a tertiary $C_{3-30}$ fluoroalkoxycarbonylalkoxy group, or (iv) a $C_{2-30}$ acetal group including moiety —O—C($R^{11}R^{12}$)—O— (wherein $R^{11}R^{12}$ are each independently hydrogen or a $C_{1-30}$ alkyl group).

W may be a single bond or a group selected from —(C=O)O—, —O(C=O)—, —O($SO_2$)—, —($SO_2$)O—, —NH($SO_2$)—, —($SO_2$)NH—, —NH(CO)—, —(CO)NH—, —$SO_2$—, and —SO—. When W is a single bond, groups L and "G" are connected to each other by a single bond, and no intermediate group is present in between. In an embodiment, W may be a single bond or —(C=O)O—.

L may be a single bond or a divalent group selected from a substituted or unsubstituted $C_{1-20}$ alkylene group, a substituted or unsubstituted $C_{1-20}$ heteroalkylene group, a substituted or unsubstituted $C_{3-20}$ cycloalkylene group, and a substituted or unsubstituted $C_{3-20}$ heterocycloalkylene group, a substituted or unsubstituted $C_{6-20}$ arylene group, and a substituted or unsubstituted $C_{7-20}$ aralkylene group. When L is a single bond, groups Y and W are connected to each other by a single bond, and no intermediate group is present in between. In an embodiment, L may be a single bond or a group having formula —$(CH_2)_{n1}$—$(CR^2R^3)_{n2}$—, wherein $R^2$ and $R^3$ are selected from hydrogen and fluorine, provided that at least one of $R^2$ and $R^3$ in each —($CR^2R^3$)— is fluorine, n1 is an integer of 0 to 10, and n2 is an integer of 1 to 10.

Y is an anionic group, which may be $SO_3$, $CO_2$, $NHSO_3$, or O.

G+ represents a cationic portion of the photoacid generator compound having formula (I). In an embodiment, G+ may have formula (III), (IV), or (V):

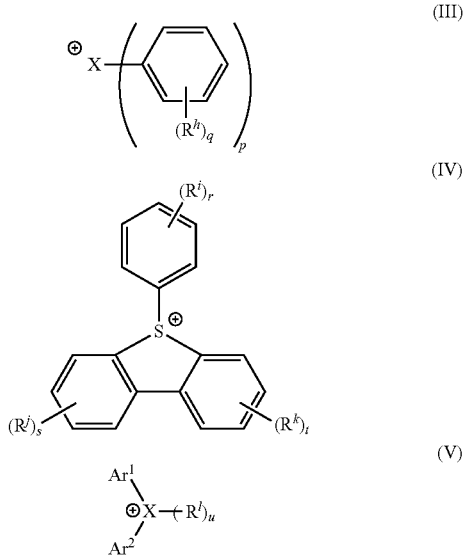

wherein
X is I or S,
$R^h$, $R^i$, $R^j$, $R^k$ and $R^l$ are unsubstituted or substituted and are each independently hydroxy, nitrile, halogen selected from fluorine, chlorine, bromine, and iodine, a $C_{1-30}$ alkyl group, a $C_{1-30}$ fluoroalkyl group, a $C_{3-30}$ cycloalkyl group, a $C_{1-30}$ fluorocycloalkyl group, a $C_{1-30}$ alkoxy group, a $C_{3-30}$ alkoxycarbonylalkyl group, a $C_{3-30}$ alkoxycarbonylalkoxy group, a $C_{3-30}$ cycloalkoxy group, $C_{5-30}$ a cycloalkoxycarbonylalkyl group, a $C_{5-30}$ cycloalkoxycarbonylalkoxy group, a $C_{1-30}$ fluoroalkoxy group, a $C_{3-30}$ fluoroalkoxycarbonylalkyl group, a $C_{3-30}$ fluoroalkoxycarbonylalkoxy group, a $C_{3-30}$ fluorocycloalkoxy group, a $C_{5-30}$ fluorocycloalkoxycarbonylalkyl group, a $C_{5-30}$ fluorocycloalkoxycarbonylalkoxy group, a $C_{6-30}$ aryl group, a $C_{6-30}$ fluoroaryl group, a $C_{6-30}$ aryloxy group, a $C_{6-30}$ fluoroaryloxy group, or a $C_{2-30}$ acetal group comprising —O—C($R^{11}R^{12}$)—O— (wherein $R^{11}$ and $R^{12}$ are each independently hydrogen or a $C_{1-30}$ alkyl group), each of which is unsubstituted or substituted;

wherein at least one of $R^i$, $R^j$, $R^k$ and $R^l$ is optionally substituted with an acid-sensitive group, a polymerizable group, or a combination thereof;

$Ar^1$ and $Ar^2$ are independently $C_{10-30}$ fused or singly bonded polycyclic aryl groups;

wherein X is S or I;
p is an integer of 2 or 3,
wherein when X is I, p is 2, and wherein when X is S, p is 3,
q and r are each independently an integer from 0 to 5,
u is an integer from 0 to 1, wherein when u is 0, X is I, and wherein when u is 1, X is S, and
s and t are each independently an integer from 0 to 4.

In formula (II), when X is S, one of the $R^c$ is optionally attached to one adjacent $R^c$ to form a ring.

In formulae (III), (IV), or (V), at least one of $R^h$, $R^i$, $R^j$, and $R^k$ may be an acid-cleavable group. In an embodiment, the acid-cleavable group may be (i) a tertiary $C_{1-30}$ alkoxy (for example, a tert-butoxy group), a tertiary $C_{3-30}$ cycloalkoxy group, a tertiary $C_{1-30}$ fluoroalkoxy group, (ii) a tertiary $C_{3-30}$ alkoxycarbonylalkyl group, a tertiary $C_{5-30}$ cycloalkoxycarbonylalkyl group, a tertiary $C_{3-30}$ fluoroalkoxycarbonylalkyl group, (iii) a tertiary $C_{3-30}$ alkoxycarbonylalkoxy group, a tertiary $C_{5-30}$ cycloalkoxycarbonylalkoxy group, a tertiary $C_{3-30}$ fluoroalkoxycarbonylalkoxy group, or (iv) a $C_{2-30}$ acetal group including moiety —O—C($R^{11}R^{12}$)—O— (wherein $R^{11}R^{12}$ are each independently hydrogen or a $C_{1-30}$ alkyl group).

Also, in formulae (III), (IV), or (V), at least one of $R^h$, $R^i$, $R^j$, and $R^k$ may be a polymerizable group. A polymerizable group may be a group including a carbon-carbon double bond or carbon-carbon triple bond. In an embodiment, the polymerizable group may include as part or all of its structure $C_{2-12}$ alkenyl, $C_{2-12}$ alkynyl, acryloyl, 2-($C_{1-12}$-alkyl)acryloyl, 2-($C_{1-12}$-fluoroalkyl)acryloyl, 2-cyanoacryloyl, or 2-fluoroacryloyl.

The photoacid generator compound having formula (I) may include both an acid-cleavable group and a polymerizable group.

The photoacid generator compound having formula (I) may include at least two iodine atoms, which may be located in the cation, the anion, or both. In formula (II), when X is S (i.e., when the cation is a sulfonium cation), the photoacid generator compound may include at least two iodine atoms. The at least two iodine atoms may be located in the sulfonium cation, the anion, or both. In formula (II), when X is I (i.e., when the cation is an iodonium cation), the photoacid generator compound may include at least one iodine atom in addition to the positively charged iodine atom of the iodonium cation. The at least one iodine atom may be located in the iodonium cation, the anion, or both. In some embodiments, the photoacid generator compound may include 2, 3, 4, 5, 6, 7, 8, 9, or 10 iodine atoms. In other embodiments, $G^+$ may include one, two, three, four, or five iodine atoms.

Specific examples of the anionic portion of the monomer having formula (I) may be represented by the following chemical formulae:

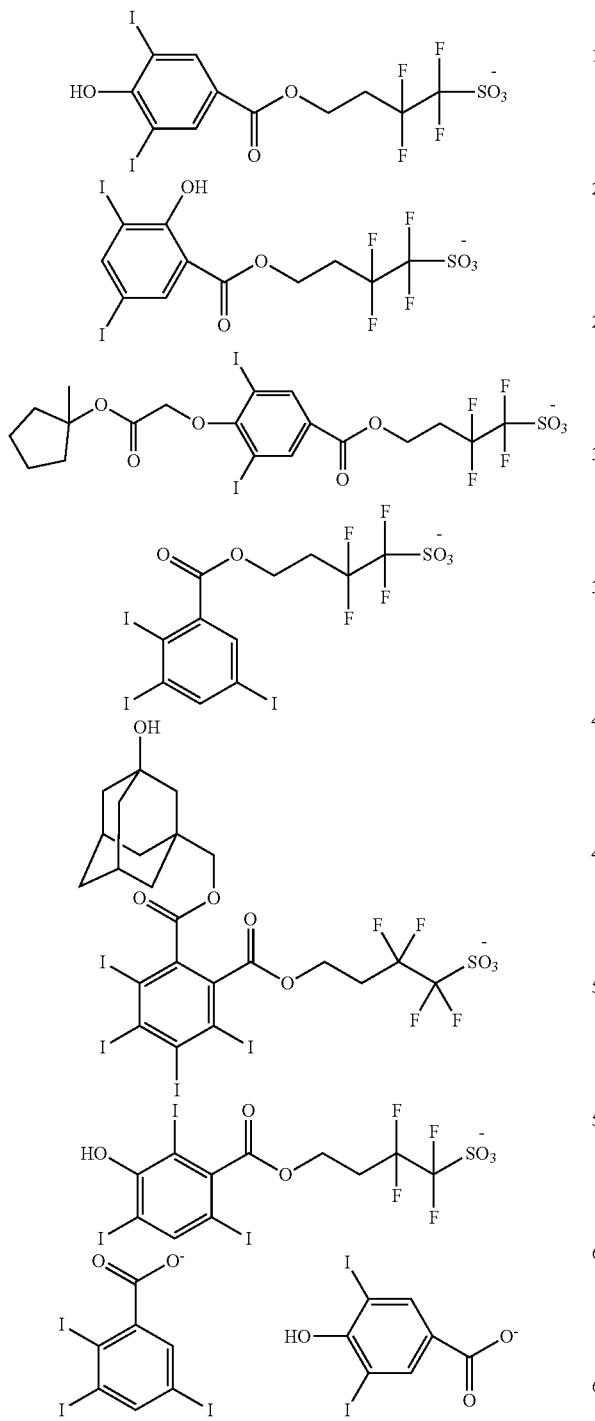

-continued

Specific examples of the cationic portion of the monomer having formula (I) may be represented by the following chemical formulae:

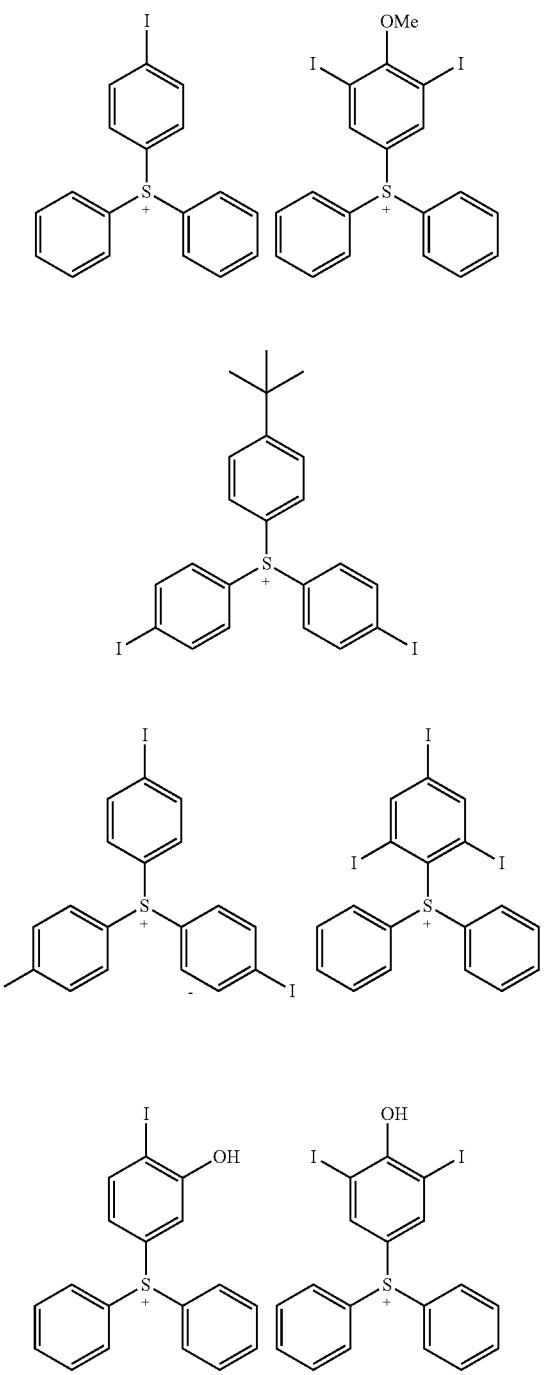

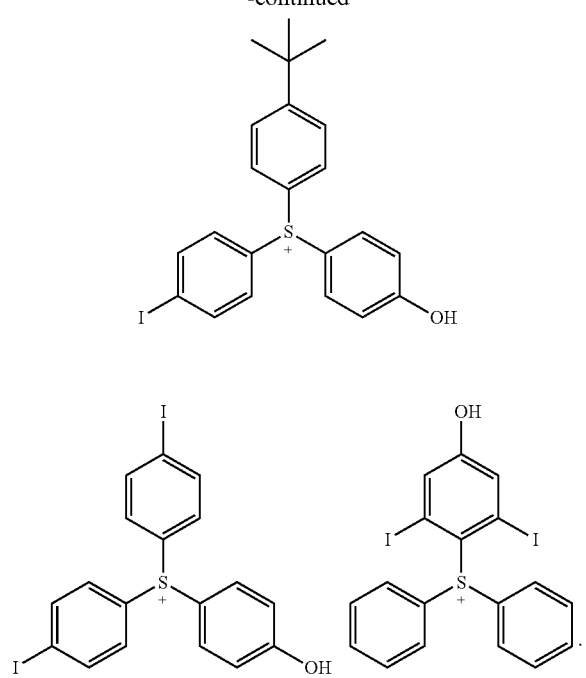
Specific examples of the monomer having formula (I) may be represented by the following chemical formulae, but are not limited thereto:
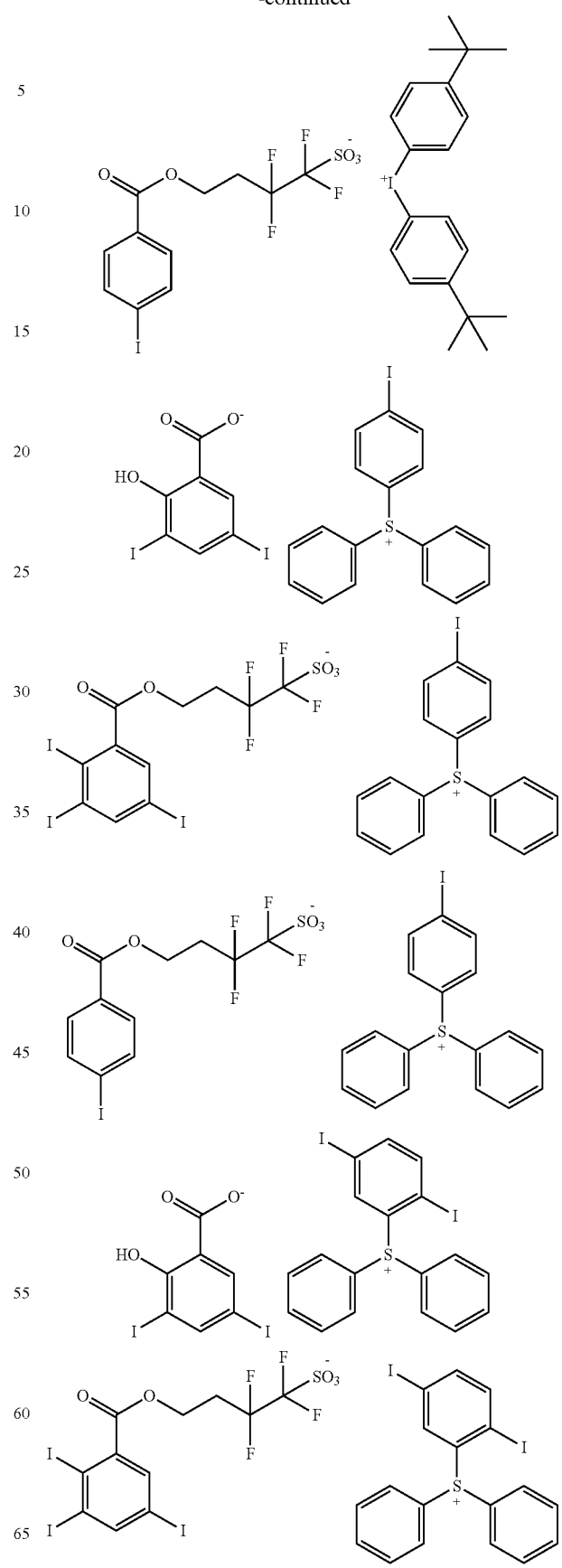

-continued

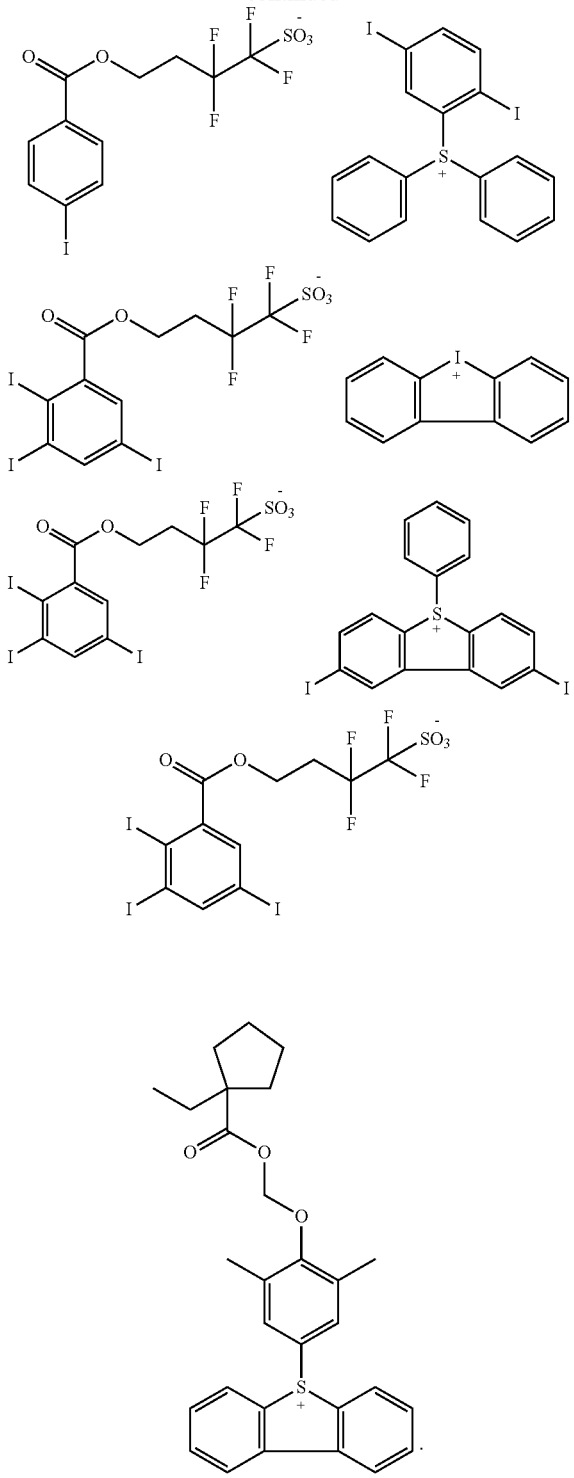

An embodiment of the present disclosure provides a photoresist composition including the above photoacid generator compound and a copolymer. The copolymer may include the acid-deprotectable monomer represented, the base-soluble monomer, and the lactone-containing monomer.

The acid-deprotectable monomer may be represented by formula (II):

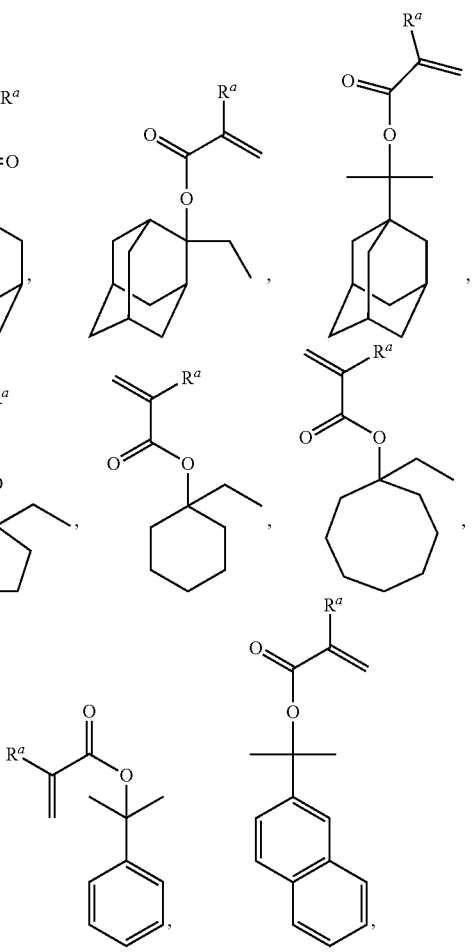

In the formula (VI), $R^b$ may independently be H, an unsubstituted or substituted $C_{1-20}$ alkyl, an unsubstituted or substituted $C_{3-20}$ cycloalkyl, an unsubstituted or substituted $C_{6-20}$ aryl, or an unsubstituted or substituted $C_{7-20}$ aralkyl, and each $R^b$ may be separate or at least one $R^b$ may be bonded to an adjacent $R^b$ to form a cyclic structure. In an embodiment, the tertiary group including $R^b$ in formula (VI) may be a t-butyl group. In another embodiment, the formula (VI) may include cycloalkyl structures, which incorporate two or more $R^b$ groups, such as 1-methylcyclopentyl, 1-ethylcyclopentyl, and 1-methylcyclohexyl, and the like.

Exemplary acid deprotectable monomers of the formula (VI) may include:

or a combination including at least one of the foregoing, wherein $R^a$ is H, F, $C_{1-6}$ alkyl, or $C_{1-6}$ fluoroalkyl.

The base-soluble monomer may be represented by formula (VII):

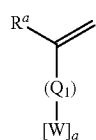

(VII)

In the formula (VII), $Q_1$ may be an ester-containing or non-ester containing group selected from an unsubstituted or substituted $C_{1-20}$ alkyl, an unsubstituted or substituted $C_{3-20}$ cycloalkyl, an unsubstituted or substituted $C_{6-20}$ aryl, and an unsubstituted or substituted $C_{7-20}$ aralkyl group. In an embodiment, where an ester is included, the ester may form a connective link between $Q_1$ and the point of attachment to the double bond. In this way, where $Q_1$ is an ester group, the formula (VII) may be a (meth)acrylate monomer. In another embodiment, where an ester is not included, $Q_1$ may be aromatic, so that the formula (VII) may be, for example, a styrenic monomer or vinyl naphthoic monomer. $Q_1$ may be fluorinated or non-fluorinated. Further in the formula (VII), a may be an integer of 1 to 3, for example, a may be 1 or 2.

Also in the formula (VII), W may be a base-reactive group comprising at least one selected from —C(=O)—OH; —C(CF$_3$)$_2$OH; —NH—SO$_2$—Y$^1$ where Y$^1$ may be F or $C_{1-4}$ perfluoroalkyl; —OH; and an adduct of any of the foregoing with a vinyl ether. In an embodiment, where $Q_1$ is non-aromatic (e.g., where formula (VII) includes a (meth) acrylate structure having an ester linked alkyl or cycloalkyl group $Q_1$), W may be —C(CF$_3$)$_2$OH. In another embodiment, where $Q_1$ is aromatic (e.g., where $Q_1$ is either ester-linked or non-ester linked and is an aromatic group such as phenyl or naphthyl), W may be OH or —C(CF$_3$)$_2$OH. It is contemplated that any of the base-reactive groups may further be protected by an acid decomposable acetal leaving group (e.g., having a generic structure —O—CH(R')—O—R" where R' may be a methyl, ethyl, or other alkyl group) Such groups are adducts of a vinyl ether, such as, for example, ethyl vinyl ether, propyl vinyl ether, t-butyl vinyl ether, cyclohexylvinyl ether, the 2-vinyloxyethyl ester of 1-adamantane carboxylic acid, 2-naphthoyl ethyl vinyl ether, or other such vinyl ethers.

Exemplary base-soluble monomers having the formula (VII) may include:

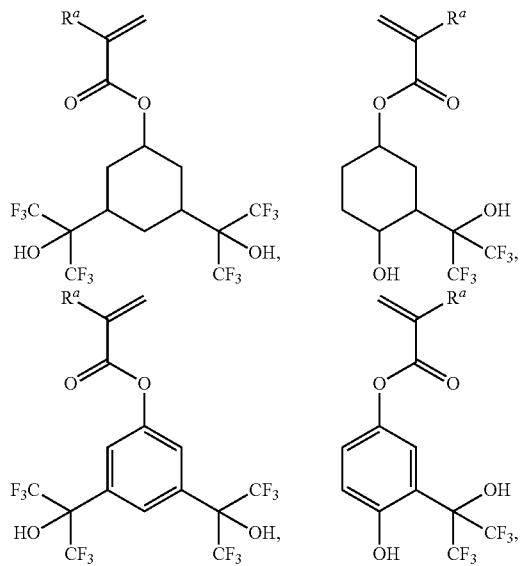

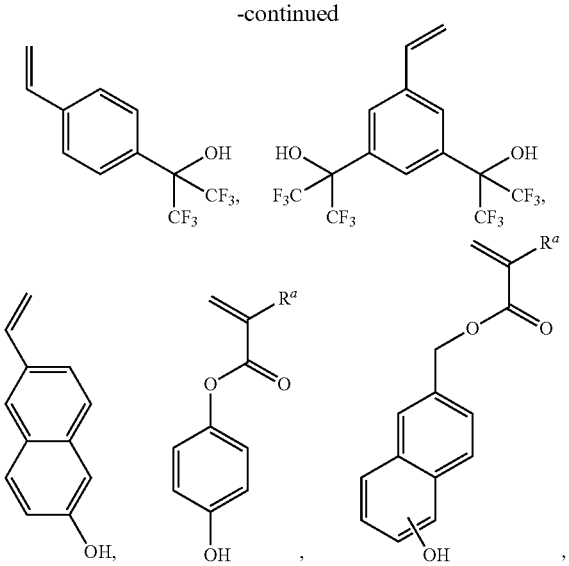

or a combination comprising at least one of the foregoing, wherein $R^a$ may be H, F, $C_{1-6}$ alkyl, or $C_{1-6}$ fluoroalkyl.

The lactone-containing monomer may be represented by formula (VIII):

In formula (VIII), L may be a monocyclic, polycyclic, or fused polycyclic $C_{4-20}$ lactone-containing group. Such lactone groups may be included to improve both adhesion of the polymer to a substrate, and to moderate the dissolution of the polymer in a base developer. In an embodiment, L may be a monocyclic $C_{4-6}$ lactone which is attached to a (meth)acrylate moiety through a monocycle ring carbon; or L may be a $C_{6-10}$ fused polycyclic lactone based on a norbornane-type structure.

In an embodiment, a lactone-containing monomer may have formula (VIIIa):

(VIIIa)

wherein
$R^a$ may be H, F, $C_{1-6}$ alkyl, or $C_{1-6}$ fluoroalkyl, R is a $C_{1-10}$ alkyl, cycloalkyl, or heterocycloalkyl, and
w may be an integer of 0 to 6.

It will be appreciated in formula (VIIIa) that R may be separate or may be attached to the lactone ring and/or one or more R groups, and that the methacrylate moiety may be attached to the lactone ring directly, or indirectly through R.

Exemplary lactone-containing monomers of formulae (VIII) and (VIIIa) may include:

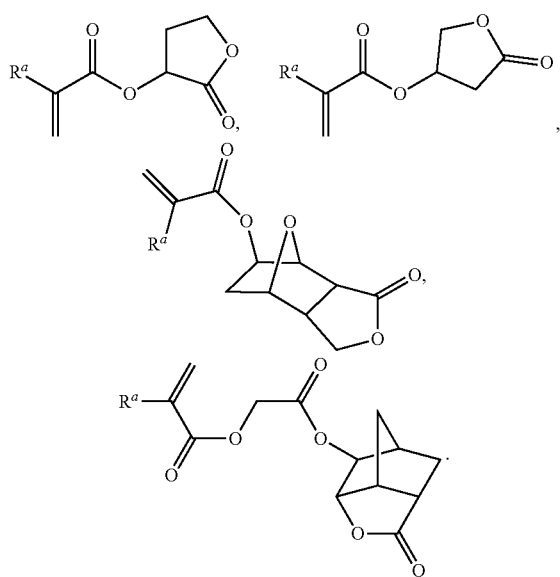

In an embodiment, the copolymer may have the following structure:

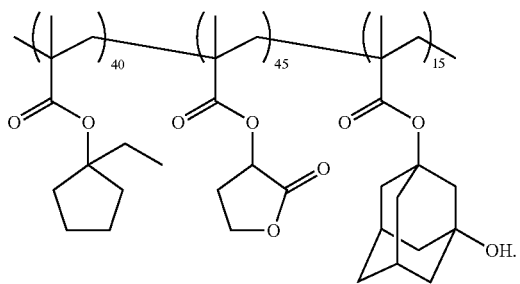

The photoresist composition including the copolymer and the photoacid generator as disclosed herein may be used to provide a layer including the photoresist. A coated substrate may be formed from the photoresist composition. Such a coated substrate includes: (a) a substrate having one or more layers to be patterned on a surface thereof; and (b) a layer of the photoresist composition over the one or more layers to be patterned.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layers on the substrates for semiconductor manufacture. Such substrates may preferably include silicon, SOT, strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying (casting) a layer of the above photoresist composition on a surface of the substrate; (b) pattern-wise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispensing, the wafer may be spun at a speed of up to 4,000 revolutions per minute (rpm), preferably from about 200 to 3,000 rpm, and more preferably 1,000 to 2,500 rpm. The coated wafer is spun to remove solvent, and baked on a hot plate to remove residual solvent and free volume from the film to make it uniformly dense.

The casting solvent can be any suitable solvent known to one of ordinary skill in the art. For example, the casting solvent can be an aliphatic hydrocarbon (such as hexane, heptane, and the like), an aromatic hydrocarbon (such as toluene, xylene, and the like), a halogenated hydrocarbon (such as dichloromethane, 1,2-dichloroethane, 1-chlorohexane, and the like), an alcohol (such as methanol, ethanol, 1-propanol, iso-propanol, tert-butanol, 2-methyl-2-butanol, 4-methyl-2-pentanol, and the like), water, an ether (such as diethyl ether, tetrahydrofuran, 1,4-dioxane, anisole, and the like), a ketone (such as acetone, methyl ethyl ketone, methyl isobutyl ketone, 2-heptanone, cyclohexanone, and the like), an ester (such as ethyl acetate, n-butyl acetate, propylene glycol monomethyl ether acetate ("PGMEA"), ethyl lactate, ethyl acetoacetate, and the like), a lactone (such as γ-butyrolactone, ε-caprolactone, and the like), a nitrile (such as acetonitrile, propionitrile, and the like), an aprotic bipolar solvent (such as dimethylsulfoxide, dimethylformamide, and the like), or a combination thereof. The choice of the casting solvent depends on a particular photoresist composition and can be readily made by one of ordinary skill in the art based on knowledge and experience.

Pattern-wise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including EUV or e-beam radiation. It will be appreciated that exposure using the activating radiation decomposes the PAG in the exposed areas and generates acid and decomposition by-products, and that the acid or the by-products then effectuates a chemical change in the polymer and nanoparticles (deblocking the acid sensitive group to generate a base-soluble group, or alternatively, catalyzing a crosslinking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is a positive tone) or removing the unexposed portions of the film (where the photoresist is crosslinkable in the exposed regions, i.e., a negative tone). Preferably, the photoresist is a negative tone, based on a polymer having pendant and/or free acid groups or by-products (derived from bound or free PAG following irradiation) that inhibit the dissolution of the nanoparticles, and the developer is preferably solvent based. A pattern forms by developing. The solvent developer can be any suitable developer known in the art. For example, the solvent developer can be an aliphatic hydrocarbon (such as hexane, heptane, and the like), an aromatic hydrocarbon (such as toluene, xylene, and the like), a halogenated hydrocarbon (such as dichloromethane, 1,2-dichloroethane, 1-chlorohexane, and the like), an alcohol (such as methanol, ethanol, 1-propanol, iso-propanol, tert-butanol, 2-methyl-2-butanol, 4-methyl-2-pentanol, and the like), water, an ether (such as diethyl ether, tetrahydrofuran, 1,4-dioxane, anisole, and the like), a ketone (such as acetone, methyl ethyl ketone, methyl isobutyl ketone, 2-heptanone, cyclohexanone, and the like), an ester (such as ethyl acetate, n-butyl acetate, propylene glycol monomethyl ether acetate ("PGMEA"), ethyl lactate, ethyl acetoacetate, and the like), a lactone (such as γ-butyrolactone, ε-caprolactone, and the like), a nitrile (such as acetonitrile, propionitrile, and the like), an aprotic bipolar solvent (such as dimethylsulfoxide, dimethylformamide, and the like), or a combination thereof. In an embodiment, the solvent developer may be a miscible mixture of solvents, for example, a mixture of an alcohol (iso-propanol) and ketone (acetone). The choice of the developer solvent depends on a particular photoresist composition and can be readily made by one of ordinary skill in the art based on knowledge and experience.

The photoresist may, when used in one or more such pattern-forming processes, be used to fabricate electronic and optoelectronic devices such as memory devices, processor chips (CPUs), graphics chips, and other such devices.

Hereinafter, the present disclosure is illustrated in more detail with reference to examples. However, these examples are exemplary, and the present disclosure is not limited thereto.

EXAMPLES

The acronyms and chemical structures of monomers used in these examples are presented in Table 1. The synthesis of the copolymer A designated PPMA/aGBLMA/DiHFA/ECPPDPS F2 (36/48/11/5) is described in U.S. Patent Publication No. US 2017/0248844 A1 by Aqad et al. The synthesis of the salt designated ECPPDBT Cl (5) was made as described in U.S. Patent Publication No. US 2014/0080058 A1 by Cameron et al. 3,5-Diiodosalycilate lithium salt was purchased from Aldrich and used as received. The salt DTBPI Ac was purchased from Heraeus Precious Metals North America Daychem LLC and used as received.

TABLE 1

| Acronym | Structure |
|---|---|
| PPMA/aGBLMA/DiHFA/ECPPDPS F2 36/48/11/5 (copolymer A) | 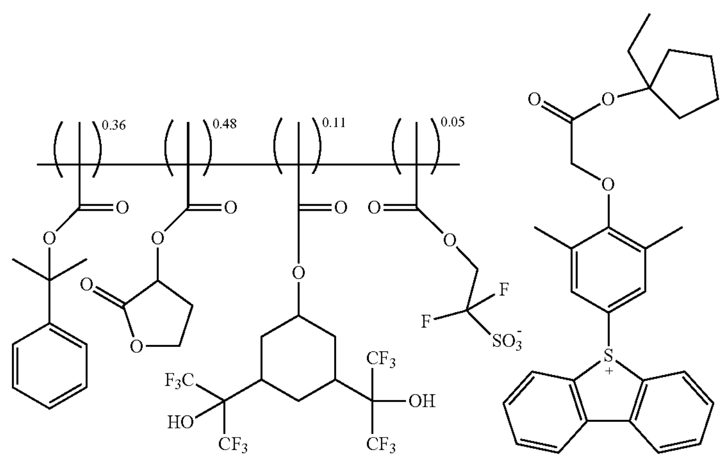 |
| ECPPDBT Cl (5) | 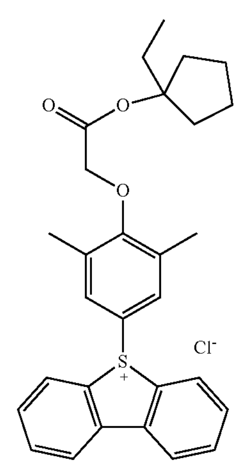 |

TABLE 1-continued

| Acronym | Structure |
|---|---|
| ECPPDBT AdOH-TFBS | (structure shown) |
| DTBPI Ac | (structure shown) |

Example 1: Photoactive Compounds Synthesis

1a) Photoacid Generator ECPPDBT TIP-TFBA

The synthetic scheme for the photoacid generator designated ECPPDBT TIP-TFBA is summarized in FIG. 1. A suspension of 2,3,5-triiodobenzoic acid (1, 25 g) in 50 ml thionyl chloride was heated at 80° C. A clear solution obtained after one hour. The heating at 80° C. was continued for an additional hour. The reaction mixture was cooled to room temperature and thionyl chloride was removed under reduced pressure. The resulting product was dissolved in toluene, and the solvent was evaporated to dryness under reduced pressure. The dry 2,3,5-triiodobenzoyl chloride was added to a solution of 11.25 g 4-bromo-3,3,4,4-tetrafluorobutanol in 100 mL of acetonitrile. Pyridine (5.20 g) was added and the mixture was stirred for 3 hours at room temperature. The solvent was evaporated to dryness under reduced pressure, and the residue was dissolved in 100 mL of dichloromethane, washed twice with 100 ml of 0.1N HCl and with 100 ml of water. The dichloromethane was removed under reduced pressure and the crude product was dissolved in 100 mL of acetonitrile. The acetonitrile solution was added to a mixture made of 17.2 g sodium dithionate and 12.5 g sodium hydrogen carbonate and the mixture was stirred at 80° C. for 16 h. The reaction was cooled to room temperature and the organic phase was separated and treated with 10 g of 30% hydrogen peroxide at 50° C. for 5 h. The acetonitrile solution was concentrated to produce the crude sodium salt TIP-TFBS (3), which was used in the next step without further purification.

The crude sodium salt TIP-TFBS (3, 8.0 g) and 0.95 equivalents of ECPPDBT Cl (5) were mixed in 100 mL of dichloromethane and 100 ml of water and stirred at room temperature for 16 h. The organic phase was separated and washed twice with 100 mL of deionized water. The solvent from the organic phase was completely removed under reduced pressure and purified by flash chromatography using dichloromethane/acetone 3/1 by volume. Fraction containing the product were combined, and the solvent was removed under reduced pressure to produce a white solid, which was dissolved in 20 ml of dichloromethane. The solution was poured into 200 ml of methyl t-butyl ether/heptane 1/1 by volume to produce 5.3 g pure photoacid generator compound ECPPDBT TIP-TFBS (10).

1b) Photoactive Quencher DTBPI DISA

Figure 2:
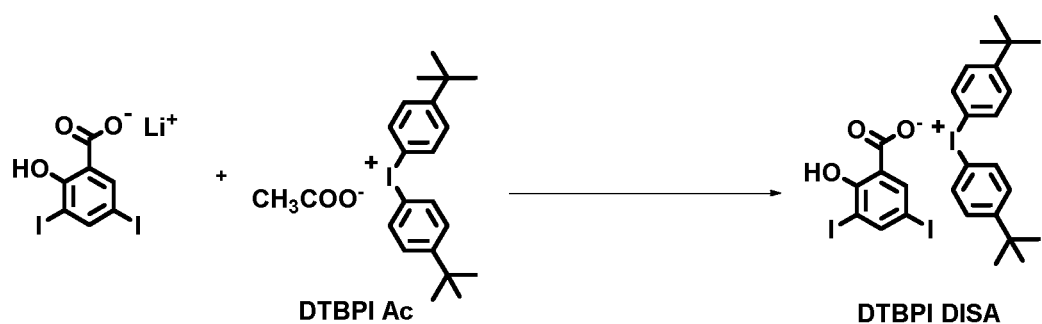
FIG. 2 is a scheme showing synthesis of the photoacid generator designated IPDPS PFBuS.

The synthetic scheme for the photoactive quencher designated DTBPI DISA is summarized in FIG. 2. A solution made of DTBPI Ac (11.4 g, 25.2 mmol) and 3,5-diiodosalycilate lithium salt (10 g, 25.26 mmol) in 100 ml of water and 100 ml of dichloromethane was stirred at room temperature for 6 h. The organic phase was separated and washed 5 times with 50 mL of deionized water. The organic phase was separated and the concentrated. The resulting residue was dissolved in 30 mL of acetone and poured into 300 mL of heptane to precipitate the product DTBPI DISA, which was filtered and dried. Yield—14.2 g.

1c) Photoacid Generator IPDPS PFBuS

Figure 3:
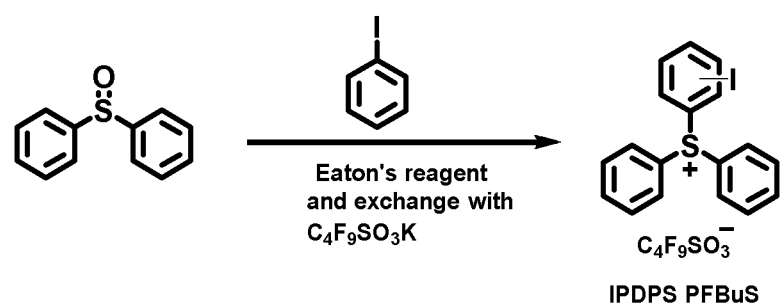
FIG. 3 is a scheme showing synthesis of the photoacid generator designated as IPDPS PFBuS.

The synthetic scheme for the photoacid generator designated as IPDPS PFBuS is summarized in FIG. 3. Diphenyl sulfoxide (10 g, 49.44 mmol) and iodobenzene (10 g, 49 mmol) were added to 100 mL of Eaton's reagent, and the mixture was stirred at room temperature overnight. The mixture was poured into 200 g of crushed ice. Non-reacted organics were extracted with methyl t-butyl ether and discarded, and 16.7 g of perfluorobutane sulfonate $C_4F_9SO_3K$ and 200 ml of dichloromethane were added to the aqueous phase. The mixture was stirred for 15 min at room temperature and the $CH_2Cl_2$ was separated and washed 5 times with 100 mL deionized water. The organic phase was collected and the solvent was evaporated to dryness under reduced pressure. The product was further dried under reduced pressure to produce the product IPDPS PFBuS. Yield—25.8 g.

1d) Photoacid Generator DTBPI 4IP-TFBS

Figure 4:
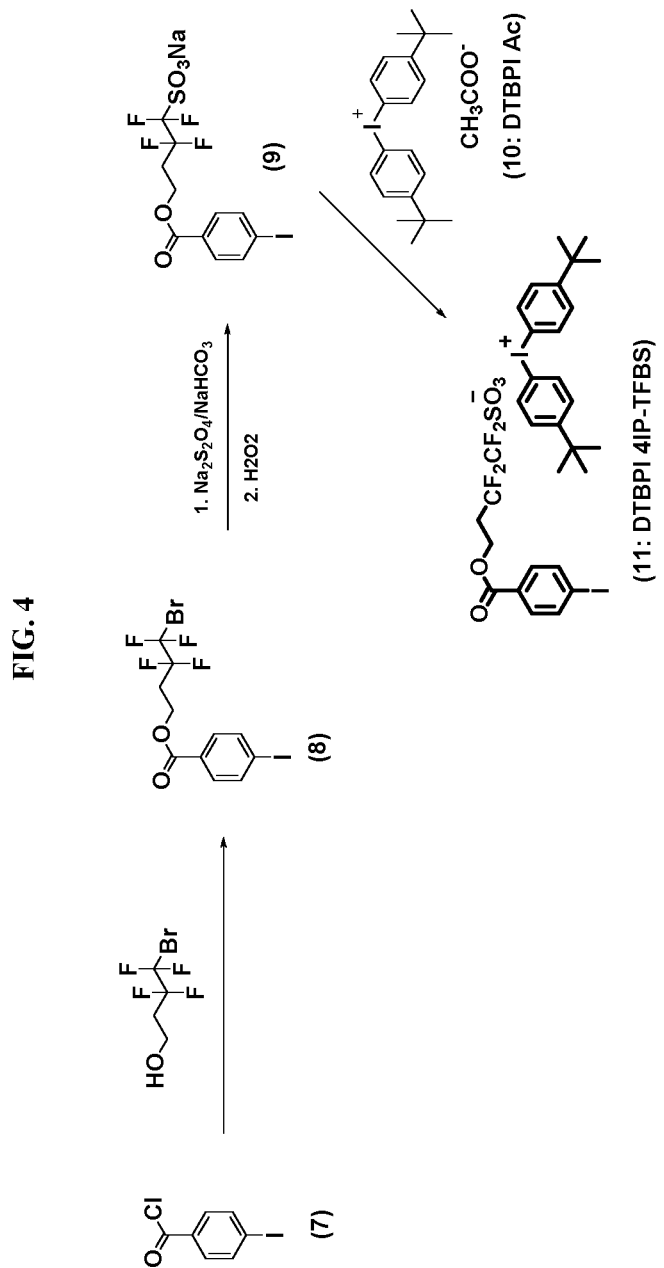
FIG. 4 is a scheme showing synthesis of the photoacid generator designated as DTBPI 4IP-TFBS.

The synthetic scheme for the photoacid generator designated as DTBPI 4IP-TFBS is summarized in FIG. 4. To a solution of 4-iodobenzoyl chloride (13.1 g, 49.16 mmol) and 4-bromo-3,3,4,4,-tetrafluorobutananol (11.0 g, 48.88 mmol) in 150 mL of tetrahydrofuran was added triethylamine (6 g), and the mixture was stirred at room temperature for 16 hours. The resulting salt was filtered, and THF tetrahydrofuran was removed completely under reduced pressure. The resulting residue was dissolved in 150 mL of dichloromethane and washed twice with 1 N aqueous solution of hydrochloric acid, followed by one wash with 100 ml of deionized water. The organic phase was separated and the solvent was completely removed to produce the product 7 as an oily residue (yield 19.5 g).

An aqueous solution made of sodium dithionate (7.5 g, 43.10 mmol) and sodium hydrogen carbonate (5.5 g, 65.5 mmol) was added to a solution of compound 7 (10 g, 22 mmol) in 200 mL of acetonitrile, and the mixture was stirred at 75° C. for 16 hours. The mixture was cooled to room temperature and the lower, aqueous layer was removed. The upper, organic layer was transferred into a flask. To the organic layer was added hydrogen peroxide (10 g of 30 weight percent solution), and the mixture was stirred at room temperature for 52 hours. The solution was filtered to remove salts, and the solvents were distilled off under reduced pressure to produce a gummy-like crude product. The crude product 9 obtained from the previous step was suspended in 100 mL of water and mixed with a suspension of DTBPI Ac (10, 7.9 g, 17.5 mmol). The resulting mixture was stirred at room temperature for 6 hours. The organic phase was separated, washed twice with 100 mL of deionized water, concentrated and poured into heptane to obtain the product DTBPI 4IP-TFBS (11) which was collected by filtration and dried. Yield 7.5 g.

Example 2: Preparation of Photoresist Composition

Formulations

Photoresist compositions containing copolymers comparative or inventive photoacid generators were each independently formulated as summarized in Table 2. Component amounts in Table 2 are based on total solids, excluding solvents. The same molar PAG loading was used in the two examples.

The quencher was trioctylamine (TOA). The surfactant was a fluorinated surfactant obtained as POLYFOX™ PF-656.

TABLE 2

| Photoresist Composition | Copolymer | PAG | Quencher | Surfactant |
|---|---|---|---|---|
| 1 (comparative) | Copolymer A | 49.0% ECPPDBT AdOH-TFBS | 2% | 0.1% |
| 2 | Copolymer A | 66.4% ECPPDBT TIP-TFBS | 2% | 0.1% |

The formulations listed in Table 2 contained a 70:30 (w/w) mixture of ethyl lactate/methyl 2-hydroxyisobutyrate as a solvent, and resists were processed at a soft bake of 110° C. for 90 seconds and a post-exposure base at 100° C. for 60 seconds.

EUV Radiation Transmission Calculations

The effect of incorporating iodine atoms into photoacid generator on film transmittance at EUV radiation (13.5 nm) is exemplified by the transmission calculation results. The transmissions at EUV exposure (13.5 nm) for the films made from photoresist compositions 1 and 2 were calculated from the Center for X-Ray Optics at Lawrence Berkeley National Laboratory web site by inputting the calculated composition molecular formula and assuming a polymer density of 1.20 g/cm$^3$ and film thickness of 60 nm. Table 2 shows the calculated % transmission of the two compositions. Composition 2 that comprise the photoacid generator ECPPDBT TIP-TFBS, according to an embodiment of the present disclosure shows lower transmittance.

Contrast Curve

Contrast curve measurements with EUV exposure source (13.5 nm) were obtained using a LithoTech Japan EUVES-9000 flood exposure tool. The resist was spin-coated onto either an organic underlayer or a silicon wafer and baked at 110° C. for 90 seconds to form a 40-50 nm thick photoresist film. The resist was exposed to an increasing dose of 13.5 nm radiation in a step-wise manner, post-exposure baked at 100° C. for 60 seconds, and developed with 0.26 N aqueous tetramethylammonium hydroxide solution for 60 seconds to form a relief image pattern of exposed and non-exposed areas. Thickness was measured at each exposed area using a KLA Thermawave-7 ellipsometer and plotted vs. dose. Dose-to-clear values ($E_0$) were calculated at 10% or less remaining film thickness. As can be seen from Table 3, photoresist composition 2, according to an embodiment of the present disclosure, exhibits smaller $E_0$ under EUV irradiation compared to photoresist composition 2, which is a comparative example.

TABLE 3

| Photoresist Composition | 13.5 nm % Transmittance at FT = 60 nm | EUV $E_0$ (mJ/cm$^2$) |
|---|---|---|
| 1 (comparative) | 71.35 | 1.5 |
| 2 | 67.64 | 1.0 |

Example 3: EUV Radiation Transmission Calculations

Figure 5:
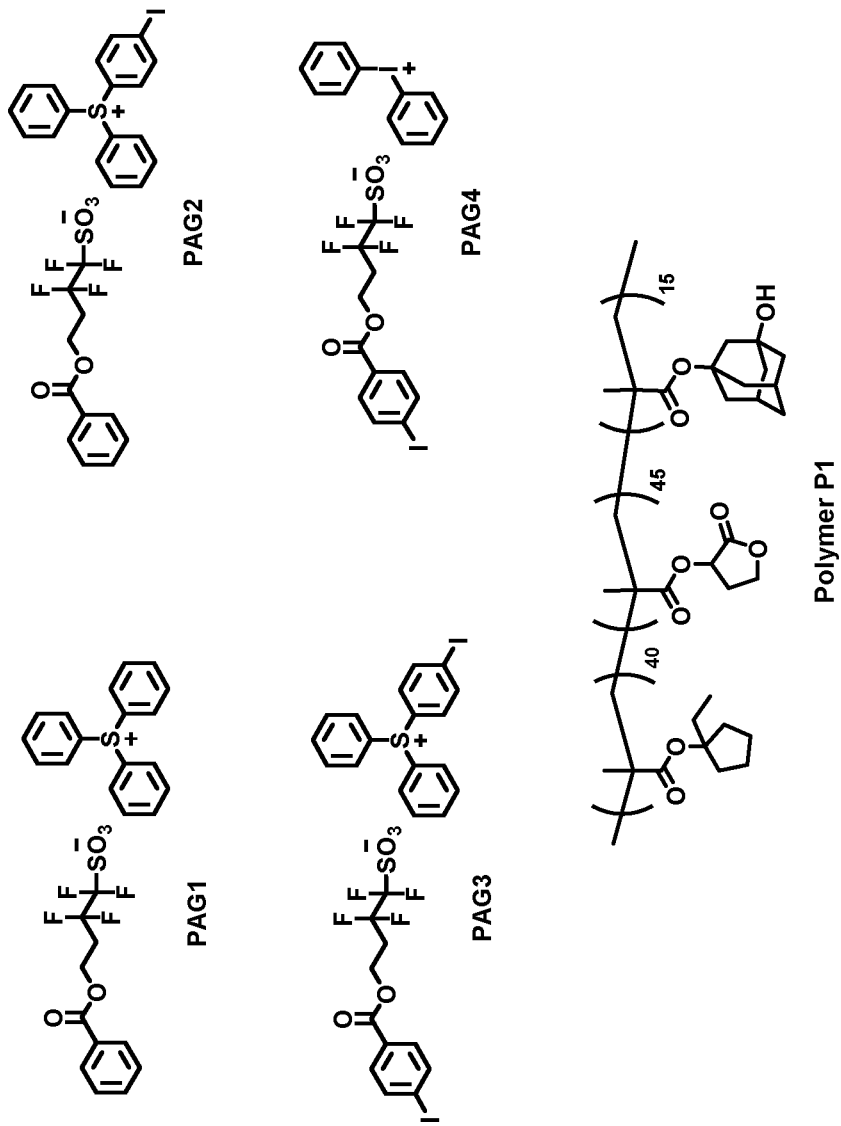
FIG. 5 shows structures of photoacid generator compounds PAG1 to PAG4 and polymer P1 described in the working examples of the present application.

The transmissions at FIN exposure (13.5 nm) for films made from composition examples were calculated from the for X-Ray Optics at Lawrence Berkeley National Laboratory web site by inputting the calculated composition molecular formula. Table 4 shows the calculated % transmissions for film made of photoactive compounds (shown in FIG. 5) at 60 nm film thickness, assuming film density of 1 g/cm$^3$.

TABLE 4

| Example | Photoacid generator | 13.5 nm % Transmittance at FT = 60 nm |
|---|---|---|
| A (Comparative) | PAG 1 | 77.06 |
| B | PAG 2 | 71.79 |
| C | PAG 3 | 68.32 |
| D | PAG4 | 66.02 |

Using these parameter, the transmission for a film made of sulfonium-containing zwitterion (DPS-PTFBS) is 76.30% and the % transmission for a film made of tellurium-containing zwitterion DPTe-PTFB is 69.20%. This indicate the less transmission or more absorption for tellurium-containing zwitterionic compounds compared to sulfur analogues.

Table 5 shows the calculated % transmission for film made of compositions that include the base polymer and a photoacid generator (P1 (shown in FIG. 5) at 60 nm film thickness, assuming film density of 1.2 g/cm³. Comparative composition C1 includes polymer P1 and the iodine free photoacid generator PAG1. The compositions I1 to I3, according to an embodiment of the present disclosure, include polymer P1 and iodine-containing photoacid generators PAG2, PAG3, and PAG4 respectively. As can be seen from Table 5, less transmission is obtained for formulations that include PAG2, PAG3, and PAG4.

TABLE 5

| Composition | Polymer | PAG | PAG mol % in composition | 13.5 nm % Transmittance at FT = 60 nm |
|---|---|---|---|---|
| C (comparative) | P1 | PAG1 | 10 | 74.18 |
| I1 | P1 | PAG2 | 10 | 72.24 |
| I2 | P1 | PAG3 | 10 | 70.53 |
| I3 | P | PAG4 | 10 | 69.89 |

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A photoacid generator compound having formula (I):

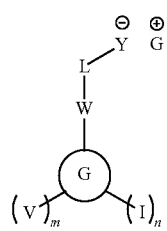

(I)

wherein, in formula (I):
"I" represents iodine;
V is $OR^1$ or $C(=O)OR^1$, wherein $R^1$ is independently H or a substituted or unsubstituted $C_{1-30}$ hydrocarbyl group optionally comprising 1 to 5 heteroatoms selected from O, S, N, P, and F, and optionally comprising an acid-cleavable group, a polymerizable group, or a combination thereof;
W is a single bond or a group selected from $-(C=O)O-$, $-O(SO_2)-$, $-(SO_2)O-$, $-NH(SO_2)-$, $-(SO_2)NH-$, $-NH(CO)-$, $-(CO)NH-$, $-SO_2-$, and $-SO-$;
m is an integer of 0 or greater;
n is an integer of 0 or greater;
L is a single bond or a group having formula $-(CH_2)_{n1}-(CR^2R^3)_{n2}-$, wherein $R^2$ and $R^3$ are selected from hydrogen and fluorine, provided that at least one of $R^2$ and $R^3$ in each $-(CR^2R^3)-$ is fluorine, n1 is an integer of 0 to 10, and n2 is an integer of 2 to 10;

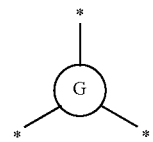

represents a monocyclic or polycyclic unsubstituted or substituted $C_{6-30}$ arylene group or a monocyclic or polycyclic unsubstituted or substituted $C_{3-30}$ heteroarylene group, wherein each "*" indicates a point of attachment to a neighboring group or atom;
$G^+$ has formula (II):

(II)

wherein, in formula (II):
X is S or I,
each $R^c$ is unsubstituted or substituted, halogenated or non-halogenated and is independently a $C_{1-30}$ alkyl group; a polycyclic or monocyclic $C_{3-30}$ cycloalkyl group; or a polycyclic or monocyclic $C_{4-30}$ aryl group,
wherein when X is S, one of the $R^c$ is optionally attached to one adjacent $R^c$ to form a ring, and the photoacid generator compound having formula (I) comprises at least two iodine atoms, and $G^+$ comprises at least one iodine, and
wherein when X is I, n is an integer of 1 or greater,
wherein when X is S, n is an integer of 0 or greater, provided the photoacid generator having formula (I) comprises at least two iodine atoms,
z is 2 or 3, wherein when X is I, z is 2, or when X is S, z is 3; and
Y is $SO_3$, $CO_2$, $NHSO_3$, or O.

2. The photoacid generator compound of claim 1, wherein W is a single bond or $-(C=O)O-$.

3. The photoacid generator compound of claim 1, wherein L a is a single bond.

4. The photoacid generator compound of claim 1, wherein

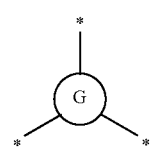

is a C$_6$ aryl group and n is 1, 2, 3, 4, or 5 when X=I, and n is 0, 1, 2, 3, 4, or 5 when X=S.

5. The photoacid generator compound of claim 1, wherein the photoacid generator compound I comprises, two, three, four, or five iodine atoms.

6. The photoacid generator compound of claim 1, wherein G$^+$ has formula (III), (IV), or (V):

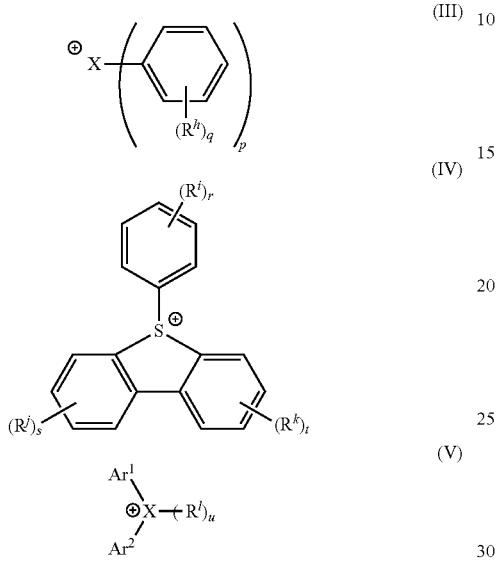

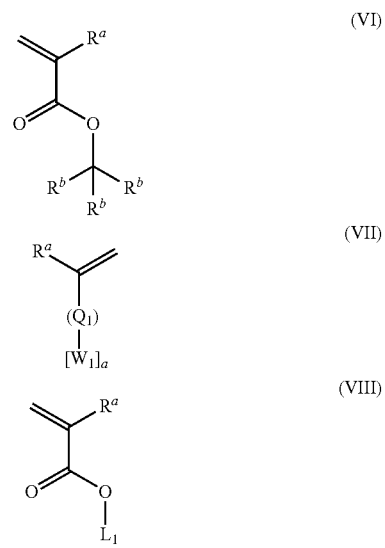

wherein each R$^a$ is independently H, F, C$_{1-10}$ alkyl, or C$_{1-10}$ fluoroalkyl;

each R$^b$ is independently H, a substituted or unsubstituted C$_{1-20}$ alkyl group, a substituted or unsubstituted C$_{3-20}$ cycloalkyl group, a substituted or unsubstituted C$_{6-20}$ aryl group, or a substituted or unsubstituted C$_{7-20}$ aralkyl group, and each R$^b$ is separate or at least one R$^b$ is bonded to an adjacent R$^b$ to form a cyclic structure;

Q$_1$ is an ester-containing or non-ester containing group selected from a substituted or unsubstituted C$_{1-20}$ alkyl group, a substituted or unsubstituted C$_{3-20}$ cycloalkyl group, a substituted or unsubstituted C$_{6-20}$ aryl group, and a substituted or unsubstituted C$_{7-20}$ aralkyl group;

W$_1$ is a base-reactive group comprising at least one selected from —C(=O)—OH; —C(CF$_3$)$_2$OH; —NH—SO$_2$—Y$^1$ where Y$^1$ is F or a C$_{1-4}$ perfluoroalkyl group; an aromatic —OH;

and an adduct of any of the foregoing with a vinyl ether;

a is an integer of 1 to 3; and

L$_1$ is a monocyclic, polycyclic, or fused polycyclic C$_{4-20}$ lactone-containing group.

X is I or S,

R$^h$, R$^i$, R$^j$, R$^k$ and R$^l$ are unsubstituted or substituted and are each independently hydroxy, nitrile, halogen selected from fluorine, chlorine, bromine, and iodine, a C$_{1-30}$ alkyl group, a C$_{1-30}$ fluoroalkyl group, a C$_{3-30}$ cycloalkyl group, a C$_{1-30}$ fluorocycloalkyl group, a C$_{1-30}$ alkoxy group, a C$_{3-30}$ alkoxycarbonylalkyl group, a C$_{3-30}$ alkoxycarbonylalkoxy group, a C$_{3-30}$ cycloalkoxy group, C$_{5-30}$ a cycloalkoxycarbonylalkyl group, a C$_{5-30}$ cycloalkoxycarbonylalkoxy group, a C$_{1-30}$ fluoroalkoxy group, a C$_{3-30}$ fluoroalkoxycarbonylalkyl group, a C$_{3-30}$ fluoroalkoxycarbonylalkoxy group, a C$_{3-30}$ fluorocycloalkoxy group, a C$_{5-30}$ fluorocycloalkoxycarbonylalkyl group, a C$_{5-30}$ fluorocycloalkoxycarbonylalkoxy group, a C$_{6-30}$ aryl group, a C$_{6-30}$ fluoroaryl group, a C$_{6-30}$ aryloxy group, a C$_{6-30}$ fluoroaryloxy group, or a C$_{2-30}$ acetal group comprising —O—C(R$^{11}$R$^{12}$)—O— (wherein R$^{11}$ and R$^{12}$ are each independently hydrogen or a C$_{1-30}$ alkyl group), each of which is unsubstituted or substituted;

wherein at least one of R$^i$, R$^j$, R$^k$ and R$^l$ is optionally substituted with an acid-sensitive group, a polymerizable group, or a combination thereof, Ar$^1$ and Ar$^2$ are independently C$_{10-30}$ fused or singly bonded polycyclic aryl groups;

wherein X is S or I;

p is an integer of 2 or 3, wherein when X is I, p is 2, and wherein when X is S, p is 3, q and r are each independently an integer from 0 to 5, u is an integer from 0 to 1, wherein when u is 0, X is I, and wherein when u is 1, X is S, and s and t are each independently an integer from 0 to 4.

7. A photoresist composition comprising the photoacid generator compound of any of claims 1 to 6 and a copolymer.

8. The photoresist composition of claim 7, wherein the copolymer comprises the acid-deprotectable monomer represented by formula (VI), the base-soluble monomer represented by formula (VII), and the lactone-containing monomer represented by formula (VIII):

9. A coated substrate, comprising: (a) a substrate having one or more layers to be patterned on a surface thereof; and (b) a layer of a photoresist composition of claim 7 over the one or more layers to be patterned.

10. A method of forming an electronic device, comprising:

(a) applying a layer of the photoresist composition of claim 7 over a surface of the substrate;

(b) pattern-wise exposing the photoresist composition layer to activating radiation; and (c) developing the exposed photoresist composition layer to provide a resist relief image.

11. A photoacid generator compound having formula (I):

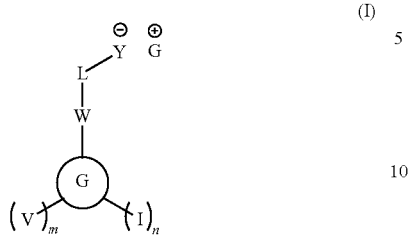

wherein, in formula (I):
"I" represents iodine;
V is $OR^1$ or $C(=O)OR^1$, wherein $R^1$ is independently H or a substituted or unsubstituted $C_{1-30}$ hydrocarbyl group optionally comprising 1 to 5 heteroatoms selected from O, S, N, P, and F, and optionally comprising an acid-cleavable group, a polymerizable group, or a combination thereof,
W is a single bond or a group selected from —(C=O)O—, —O(C=O)—, —O($SO_2$)—, —($SO_2$)O—, —NH($SO_2$)—, —($SO_2$)NH—, —NH(CO)—, —(CO)NH—, —$SO_2$—, and —SO—;
m is an integer of 0 or greater;
n is an integer of 0 or greater;
L is a single bond, an unsubstituted $C_{1-20}$ heteroalkylene group, a substituted or unsubstituted $C_{3-20}$ cycloalkylene group, a substituted or unsubstituted $C_{3-20}$ heterocycloalkylene group, a substituted or unsubstituted $C_{7-20}$ aralkylene group, or a group having formula —$(CH_2)_{n1}$—$(CR^2R^3)_{n2}$—, wherein $R^2$ and $R^3$ are selected from hydrogen and fluorine, provided that at least one of $R^2$ and $R^3$ in each —$(CR^2R^3)$— is fluorine, n1 is an integer of 0 to 10, and n2 is an integer of 1 to 10;

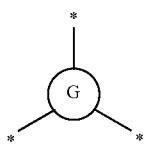

represents a monocyclic or polycyclic unsubstituted or substituted $C_{6-30}$ arylene group or a monocyclic or polycyclic unsubstituted or substituted $C_{3-30}$ heteroarylene group, wherein each "*" indicates a point of attachment to a neighboring group or atom;
$G^+$ has formula (II):

wherein, in formula (II):
X is S or I,
each $R^c$ is unsubstituted or substituted, halogenated or non-halogenated and is independently a $C_{1-30}$ alkyl group; a polycyclic or monocyclic $C_{3-30}$ cycloalkyl group; or a polycyclic or monocyclic $C_{4-30}$ aryl group,
wherein when X is S, one of the $R^c$ is optionally attached to one adjacent $R^c$ to form a ring, and the photoacid generator compound having formula (I) comprises at least two iodine atoms, and
wherein when X is I, n is an integer of 1 or greater,
wherein when X is S, n is an integer of 0 or greater, provided the photoacid generator having formula (I) comprises at least two iodine atoms,
z is 2 or 3, wherein when X is I, z is 2, or when X is S, z is 3; and
Y is $CO_2$.

12. A photoacid generator compound having formula (I):

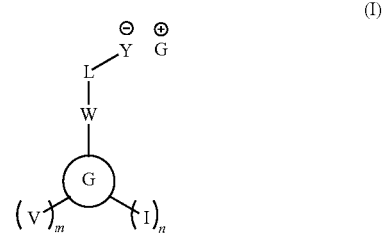

wherein, in formula (I):
"I" represents iodine;
V is $OR^1$ or $C(=O)OR^1$, wherein $R^1$ is independently H or a substituted or unsubstituted $C_{1-30}$ hydrocarbyl group optionally comprising 1 to 5 heteroatoms selected from O, S, N, P, and F, and optionally comprising an acid-cleavable group, a polymerizable group, or a combination thereof;
W is a single bond or a group selected from —(C=O)O—, —O($SO_2$)—, —($SO_2$)O—, —NH($SO_2$)—, —($SO_2$)NH—, —NH(CO)—, —(CO)NH—, —$SO_2$—, and —SO—;
m is an integer of 0 or greater;
L is a single bond or a group having formula —$(CH_2)_{n1}$—$(CR^2R^3)_{n2}$—, wherein $R^2$ and $R^3$ are selected from hydrogen and fluorine, provided that at least one of $R^2$ and $R^3$ in each —$(CR^2R^3)$— is fluorine, n1 is an integer of 0 to 10, and n2 is an integer of 2 to 10;

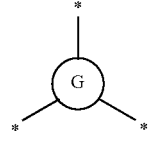

represents a monocyclic or polycyclic unsubstituted or substituted $C_{6-30}$ arylene group or a monocyclic or polycyclic unsubstituted or substituted $C_{3-30}$ heteroarylene group, wherein each "*" indicates a point of attachment to a neighboring group or atom;
$G^+$ has formula (II):

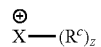

wherein, in formula (II):
X is I,
each $R^c$ is unsubstituted or substituted, halogenated or non-halogenated and is independently a $C_{1-30}$ alkyl group; a polycyclic or monocyclic $C_{3-30}$ cycloalkyl group; or a polycyclic or monocyclic $C_{4-30}$ aryl group, and n is an integer of 1 or greater, z is 2; and Y is $SO_3$, $CO_2$, $NHSO_3$, or O.

13. A photoacid generator compound having formula (I):

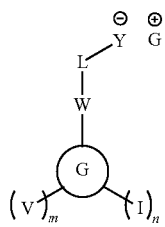

(I)

wherein, in formula (I):

"I" represents iodine;

V is $OR^1$ or $C(=O)OR^1$, wherein $R^1$ is independently H or a substituted or unsubstituted $C_{1-30}$ hydrocarbyl group optionally comprising 1 to 5 heteroatoms selected from O, S, N, P, and F, and optionally comprising an acid-cleavable group, a polymerizable group, or a combination thereof, W is a single bond or a group selected from —(C=O)O—, —O(C=O)—, —O(SO$_2$)—, —(SO$_2$)O—, —NH(SO$_2$)—, —(SO$_2$)NH—, —NH(CO)—, —(CO)NH—, —SO$_2$—, and —SO—;

m is an integer of 0 or greater;

n is an integer of 0 or greater;

L is a single bond, a substituted or unsubstituted $C_{1-20}$ alkylene group, a substituted or unsubstituted $C_{1-20}$ heteroalkylene group, a substituted or unsubstituted $C_{3-20}$ cycloalkylene group, a substituted or unsubstituted $C_{3-20}$ heterocycloalkylene group, a substituted or unsubstituted $C_{6-20}$ arylene group, or a substituted or unsubstituted $C_{7-20}$ aralkylene group;

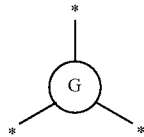

represents a monocyclic or polycyclic unsubstituted or substituted $C_{6-30}$ arylene group or a monocyclic or polycyclic unsubstituted or substituted $C_{3-30}$ heteroarylene group, wherein each "*" indicates a point of attachment to a neighboring group or atom;

$G^+$ has formula (II):

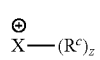

(II)

wherein, in formula (II):

X is S or I, each $R^c$ is unsubstituted or substituted, halogenated or non-halogenated and is independently a $C_{1-30}$ alkyl group; a polycyclic or monocyclic $C_{3-30}$ cycloalkyl group; or a polycyclic or monocyclic $C_{4-30}$ aryl group, wherein when X is S, one of the $R^c$ is optionally attached to one adjacent $R^c$ to form a ring, the photoacid generator compound having formula (I) comprises at least two iodine atoms, n is an integer of 1 or greater, and $G^+$ comprises at least one iodine, z is 2 or 3, wherein when X is I, z is 2, or when X is S, z is 3; and Y is $SO_3$, $CO_2$, $NHSO_3$, or O, wherein when X is I, $G^+$ comprises at least one iodine in addition to the positively charged iodonium cation.

* * * * *